United States Patent [19]

Harbaugh

[11] Patent Number: 4,655,751

[45] Date of Patent: Apr. 7, 1987

[54] LIQUID DISPENSING AND RECEIVING SYRINGE

[76] Inventor: John T. Harbaugh, 4407 Babcock Ave., Studio City, Calif. 91604

[21] Appl. No.: 829,330

[22] Filed: Feb. 14, 1986

[51] Int. Cl.$^4$ ............................................. A61M 5/32
[52] U.S. Cl. .................................................. 604/198
[58] Field of Search ............... 604/196, 197, 198, 192, 604/263

[56] References Cited

U.S. PATENT DOCUMENTS

| | | | |
|---|---|---|---|
| 2,571,653 | 10/1951 | Bastien | 604/198 |
| 2,888,924 | 6/1959 | Dunmire | 604/196 |
| 3,487,834 | 1/1970 | Smith, Jr. et al. | 604/197 |
| 4,356,822 | 11/1982 | Winstead-Hall | 604/198 |

FOREIGN PATENT DOCUMENTS 106560  9/1898  Fed. Rep. of Germany ...... 604/197

*Primary Examiner*—John D. Yasko
*Attorney, Agent, or Firm*—John J. Posta, Jr.

[57] ABSTRACT

The liquid dispensing and receiving syringe includes an elongated preferably cylindrical transparent container open at its front and rear ends and defining a central cavity for holding liquid. A rearwardly extending plunger is slideably secured in the rear end of the cavity for dispensing liquid out the front end of the container and through a hollow needle or nozzle secured to the container front end and for sucking liquid into the cavity from the needle. A concentric protective shell is connected to and spaced outwardly from the container sidewall and is slideable between a first needle-expository position and a second needle-covering position. The shell has windows and/or a grid to permit viewing of the container. A number of spacer ears spaced on the container's outer surface and/or the shell's inner surface may temporarily or permanently lock in mating pockets and/or frictionally slide in longitudinal grooves in the container outer surface. The shell may be resilient and flexible to allow temporary distortion thereof to move the ears in and out of the pockets and/or to permit breaking of the needle to disable it. The container sidewalls may include transverse scorelines to permit easy breaking of the container to prevent its reuse. The syringe is compact, disposable, inexpensive and offers improved safety.

14 Claims, 7 Drawing Figures

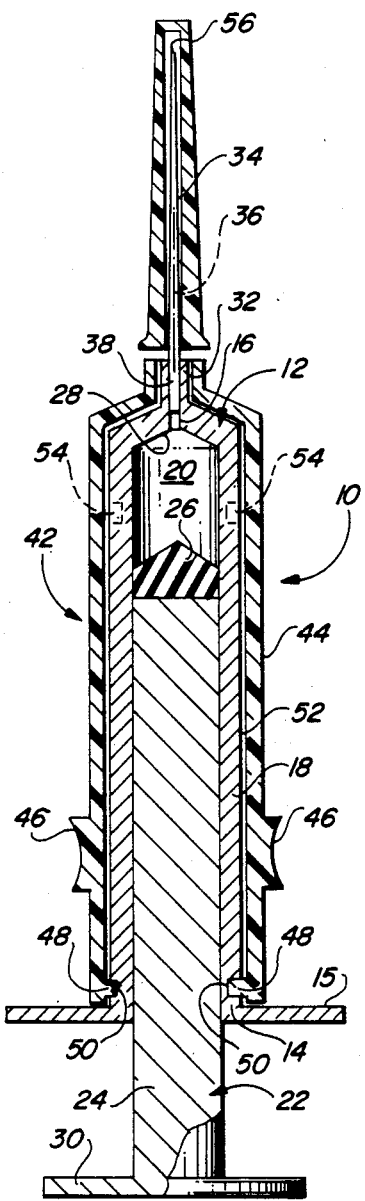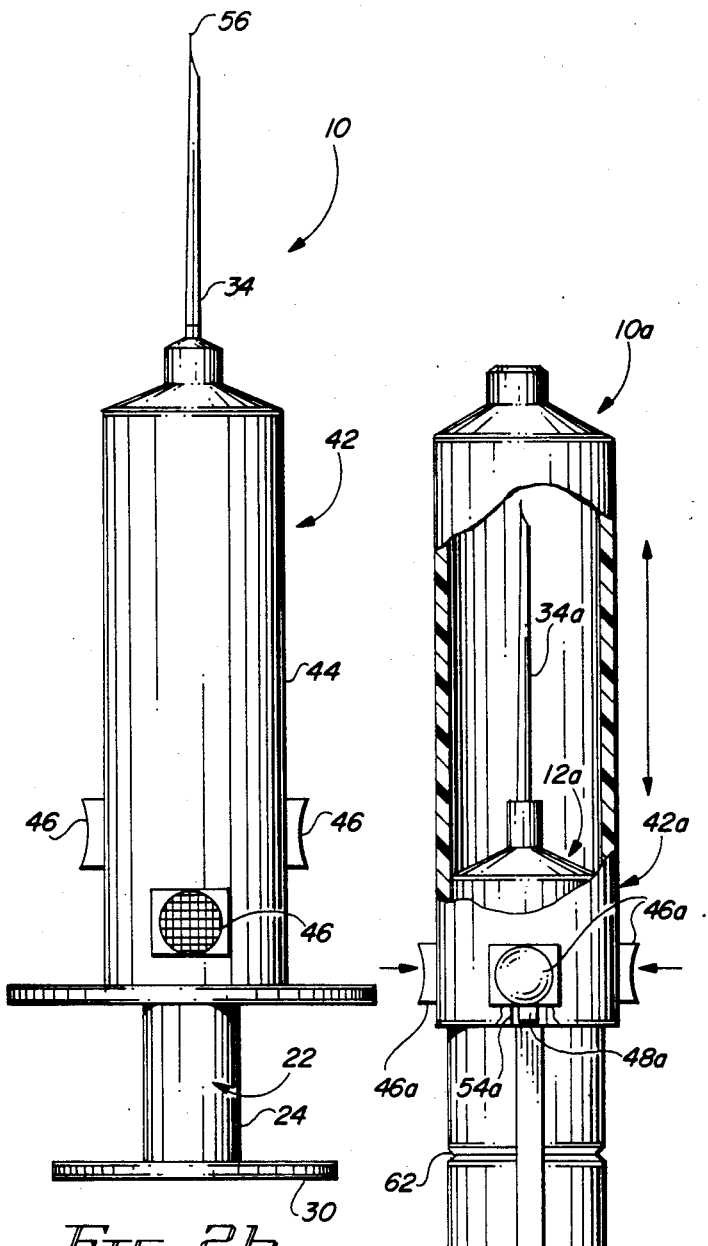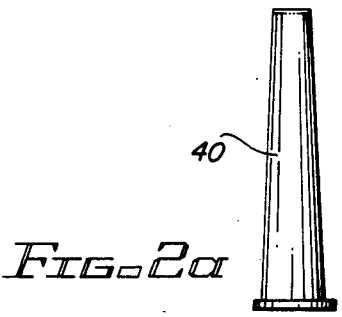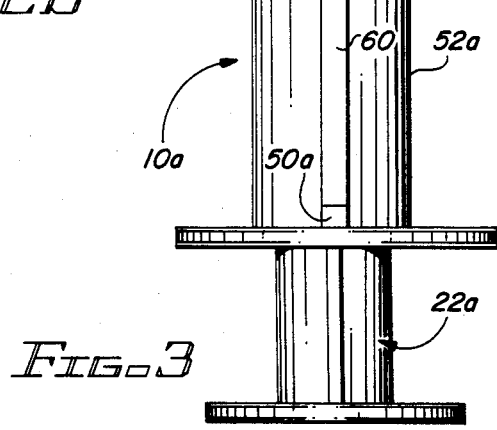
FIG. 1
FIG. 2a
FIG. 2b
FIG. 3

LIQUID DISPENSING AND RECEIVING SYRINGE

BACKGROUND OF THE INVENTION

1. Field of the Invention

The present invention generally relates to liquid dispensers and receivers and, more particularly, to an improved liquid dispensing and receiving syringe.

2. Prior Art

Syringes have been utilized on medical applications for sucking up and dispensing liquid samples, medications and the like. Efforts are being made to restrict their access to addicts. Most such syringes include a hollow container fitted with a rear plunger and a front nozzle, usually a sharp needle. Since syringes are often used in the taking of blood samples in the detection of dangeorus diseases such as aids, hepatitis, herpes and other viral and bacterial infections, the syringes are often disposable; that is, intended for a one-time use. Such a syringe can be very dangerous. It is therefore a common procedure to either break the syringe needle after use and/or tip cap it and then throw the used syringe away. However, any handling of the syringe after its initial use can be very dangerous. Infection of the handler can arise by inadvertent unintended pricking of the skin with the used needle during breaking or capping thereof. It might be noted that breaking of the syringe needle would also prevent reuse thereof by drug addicts.

Accordingly, there remains a need for an improved inexpensive needle-bearing syringe which can be safely handled after its use and which can be safely and permanently disabled to prevent its reuse.

SUMMARY OF THE INVENTION

The improved syringe of the present invention satisfies all the foregoing needs. The syringe is substantially as set forth in the Abstract of the Disclosure. Thus, it comprises a container having a liquid-receiving central cavity and open front and rear ends. A plunger is slideably disposed in the rear end of the container to suck liquid into and push it out of the cavity, while a hollow nozzle or needle is releasably or permanently secured to the front end of the container for transferring liquid to and from the cavity.

In addition, a protective concentric outer shell is slideably secured around the container for movement between a first needle-exposing position and a second needle-covering position. The shell may releasably or permanently lock in place in these positions, as by ears in pockets in the outer surface of the container and inner surface of the shell.

The container is transparent and the shell has one or more windows in it to permit viewing of the container as it is being filled with liquid and as it dispenses liquid. In one embodiment the shell comprises an open mesh grid of plastic or the like. Preferably, the container has one or more transverse grooves which, if desired, are exposed when the shell is in the second position, so that the container can be easily broken to prevent its use. Alternatively, the container can be broken while covered by the flexible shell. If desired, such grooves may also be in the shell wall and can be alignable with those of the container to allow both the shell and container to be readily broken together, particularly if the shell and container are rigid.

Further features of the improved syringe of the present invention are set forth in the following detailed description and accompanying drawings.

DRAWINGS

FIG. 1 is a schematic vertical cross-section of a first preferred embodiment of the improved syringe of the present invention;

FIG. 2 is a schematic front elevation of the syringe of FIG. 1, showing the needle cap in FIG. 2a and the remainder of the syringe in FIG. 2b;

FIG. 3 is a schematic front elevation, partly broken away, of a second preferred embodiment of the improved syringe of the present invention;

DETAILED DESCRIPTION

Figure 4:
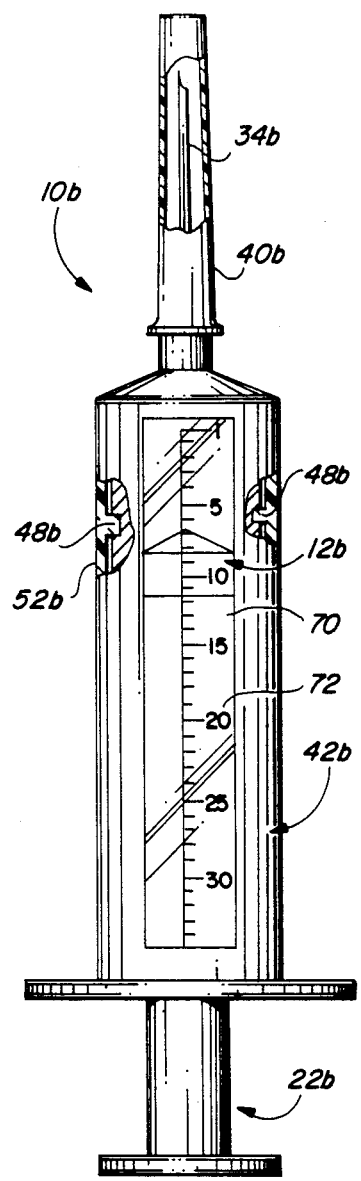
FIG. 4 is a schematic front elevation, partly broken away, of a third preferred embodiment of the improved syringe of the present invention.

FIGS. 1 and 2.

Now referring more particularly to FIGS. 1 and 2 of the accompanying drawings, a first preferred embodiment of the improved syringe of the present invention is schematically shown therein in vertical cross-section in FIG. 1 and in elevation in FIG. 2. Thus, syringe 10 is shown, which comprises an elongated generally cylindrical container or Tube 12 of transparent plastic or glass or the like having an open rear end 14 with transverse rear flange 15, an open front end 16 and a sidewall 18 defining therewith a central liquid storage space 20.

An elongated cylindrical plunger 22 of metal, plastic, glass or the like is slideably received into space 20 through end 14. Plunger 22 includes a plunger shaft 24 with a generally cone-shaped front tip 26, preferably of flexible resilient, plastic rubber or the like and configured to conform to the interior front portion 28 of tube 12. Plunger 22 also includes a rear transverse handle 30.

Front end 16 of tube 12 is necked down to a forwardly extending narrow diameter neck portion 32 to which the rear end of a tapered needle 34 is releasably or permanently secured. Needle 34 projects forward of tube 12 and has a central passageway 36 the length thereof aligned with a similar passageway 38 in neck 32, in turn communicating with cavity 20.

Needle 34 may initially be covered by a removable cap 40 for sanitary purposes. Of more importance, syringe 10 contains a protective shell 42 spaced outwardly from, concentric with and slideably connected to tube 12. Shell 42 may be of a suitable flexible, resilient deformable rubber, plastic or the like and generally conforms to the shape of the outside of tube 12. It includes means to view the contents of tube 12. Thus, it may be transparent or include windows (not shown), etc. Moreover, the outer surface 44 of shell 42 bears spaced finger grips 46 for sliding shell 42 relative to tube 12, and a pair of spaced inwardly directed ears 48 releasably disposed in a pair of pockets 50 in the outer surface 52 of tube 12 at rear end 14 thereof. A similar pair of pockets 54 may be provided in surface 52 adjacent the front end 16 thereof. In the position shown in FIG. 1, shell 42 is locked rearwardly of needle 34, so that when cap 40 is removed, needle 34 is exposed and ready for use.

When cap 40 is so removed and needle 34 thus exposed, syringe 10 can be used in the conventional way, as by advancing plunger 22 all the way forward to expel air from cavity 20, then placing the tip 56 in a liquid source (blood, an aqueous drug solution or the like, then retracting plunger 22 to suck the liquid into cavity 20 to the amount desired, then later advancing plunger 22 again to fully expel the liquid from syringe 10.

After such use, shell 42 can be flexed by the fingers to oval its shape and thus withdraw ears 48 from pockets 50, after which shell 42 can be slid forward with ears 48 riding on surface 52 until they drop into pockets 54, permanently or releasably locking shell 42 forward over needle 34 to fully cover it. Thus, after its use, needle 34 is protected without having to reseat cap 40 on tip 56 of needle 34, a dangerous procedure, and also without having to touch any part of needle 34 or neck 34. Syringe 10 in the shell forward-locked position can now be disposed of without any danger. Thus, syringe 10 is improved in safety and convenience over conventional syringes.

FIGS. 3 through 6 schematically depict, respectively, syringes 10a, 10b, 10c and 10d. Components thereof similar to those of syringe 10 bear the same numerals, but are succeeded by, respectively, the letters "a", "b", "c", and "d".

FIG. 3.

Syringe 10a is substantially identical to syringe 10, but has slightly different proportions than syringe 10 and is not shown with its needle cap. It operates the same and has the advantages of syringe 10. Thus, it includes tube 12a with needle 34a and plunger 22a, and concentric outer shell 42a with finger grips 46a. It also includes one or more ears 48a releasably receivable in pockets 50a and 54a at opposite ends of an ear-receiving slide groove 60 shallower than pockets 50a and 54a, for easy advancing, retracting and locking of shell 42a relative to tube 12. In addition, tube 12 has a transversely extending circumferential groove or score line 62 in its outer surface 52a to readily permit tube 12a to be snapped apart, that is, broken after use to prevent its reuse.

FIG. 4.

In FIG. 4, syringe 10b is shown to be substantially identical to plunger 10, except that shell 42b has a large window 70 therein through which to readily view tube 12b, markings 72 thereon and the contents of tube 12b. Plunger 22b, cap 40b and needle 34b are identical to their counterparts in plunger 10. A single spaced pair of ears 48b secured to surface 52b separate shell 42b from tube 12. Syringe 10b has substantially the advantages of syringe 10.

FIG. 5.

Figure 5:
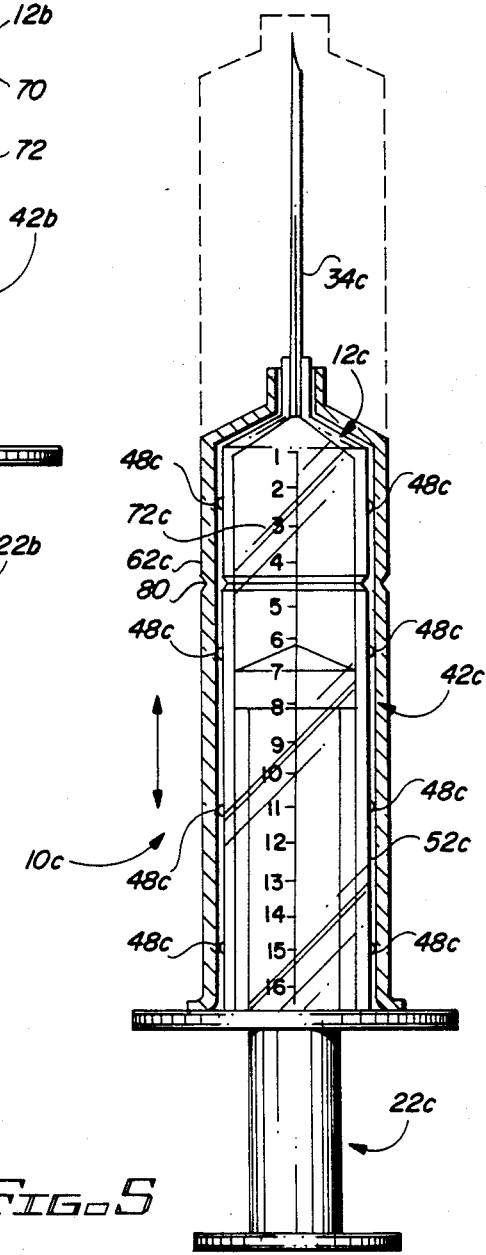
FIG. 5 is a schematic front elevation of a fourth preferred embodiment of the improved syringe of the present invention; and, FIG. 6 is a schematic front elevation of a fifth preferred embodiment of the improved syringe of the present invention.

In FIG. 5, syringe 10c is shown to be substantially identical in configuration and advantages to syringe 10, except that syringe 10c's cap is not shown. Moreover, both tube 12c and shell 42c are transparent and rigid as, for example, of glass or clear plastic, and both contain alignable transverse grooves or score lines 62c (tube 12c) and 80 (shell 42c) permitting them to be broken or snapped apart easily, rendering syringe 10c non-reuseable. Plunger 22c and needle 34c are identical to plunger 22 and needle 34. Graduated markings 72c on surface 52c are clearly visible. However, there are no pockets such as 50 and 54 of syringe 10. Instead, there are four pairs of spaced ears 48c of resilient rubber, plastic or the like, secured to surface 52c of tube 12c to space shell 42c therefrom, but permit frictional sliding of shell 42c over tube 12c with automatic position retention therebetween. The forward position of shell 42c is shown in dotted outline.

FIG. 6.

Figure 6:
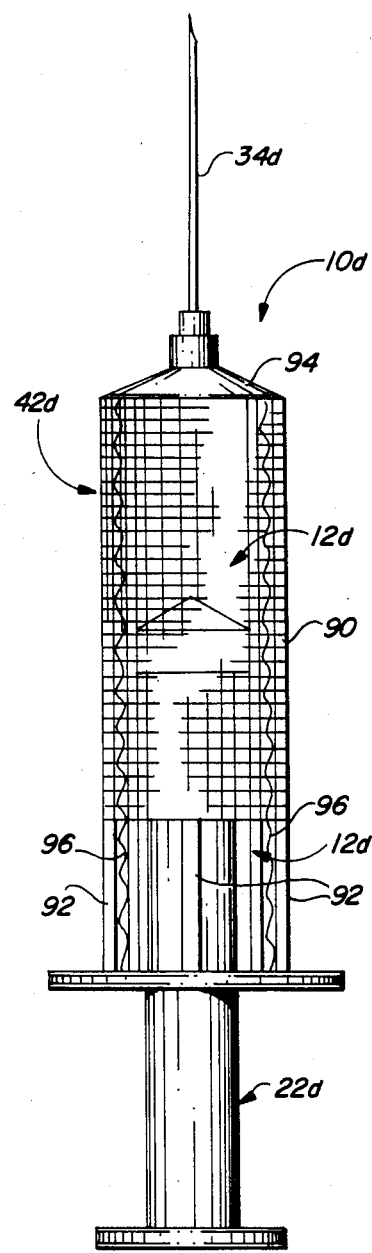

In FIG. 6, syringe 10d is shown to be substantially identical to syringe 10, except that syringe 10d's cap is not shown, and shell 42d is in the form of an open-plastic mesh or screen 90 supported by rear leg struts 92 and connected to a solid front crown 94. Tube 12d is easily viewable through screen 90 and is shown to be spaced from screen 90 by a spaced pair of undulating strips 96 connected to the outer surface 52d of tube 12d so that shell 42d can slide thereover. Plunger 22d and needle 34d are identical to plunger 22 and needle 34. Syringe 10d has substantially the advantages of syringe 10.

Various other modifications, changes, alterations and additions can be made in the improved syringe of the present invention, its components and their parameters. All such changes, modifications, alterations and additions as are within the scope of the appended claims form part of the present invention.

What is claimed is:

1. An improved liquid receiving and dispensing syringe, said syringe comprising, in combination:
   (a) an elongated container open at its front and rear ends and containing sidewalls defining a generally central cavity adapted to hold a dispensible liquid;
   (b) an elongated needle containing a central longitudinal liquid-dispensing passageway extending thoughout the length thereof, said needle being the front end of said container and extending forwardly therefrom, said needle being in communication with said container cavity for delivery of liquid therefrom and thereinto;
   (c) the plunger slideably disposed in said cavity extending rearwardly from the rear end of said container and adapted to force liquid forwardly from said cavity out through said needle, and to such liquid into said cavity; and
   (d) a protective shell connected to, slideably disposed around and normally spaced outwardly from said container sidewalls, and movable between a first rear position exposing said needle and a second front position concealing said needle to prevent inadvertent injury by contact with said needle and to facilitate disposal of said syringe,
   (e) wherein spacer means are secured to at least one of the inner surface of said shell and the outer surface of said container to facilitate at least one of the functions of releasably locking said shell in at least one of said first and second positions and sliding said shell between said first and second positions,
   (f) wherein said spacer means comprises a plurality of inwardly directed ears projecting from the inner surface of said shell,
   (g) said container having a plurality of retaining pockets on the outside surface thereof near both the front end and the rear end of said container,
   (h) said ears being releasably receivable within said retaining pockets within the outer surface of said container, whereby said ears are positioned within the pockets at the rear end of the container when the needle is not covered by said shell, and whereby said ears are positioned within the pockets at the front end of said container when the needle is covered by said shell, such ears and pockets serving to inter-lock the container and the shell to prevent relative movement thereof.

2. The improved syringe of claim 1 wherein two pairs of said pockets are spaced along the length of said container outer surface and are interconnected by longitudinal grooves within which said ears are slideable.

3. The improved syringe of claim 1 wherein the outer surface of said shell contains finger grips to facilitate movement of said shell between said first and second positions and to deform said shell.

4. The improved syringe of claim 1 wherein said shell includes means for viewing said container disposed therewithin.

5. The improved syringe of claim 4 wherein said container and said shell are transparent and generally cylindrical.

6. The improved syringe of claim 4 wherein said container is transparent and wherein said shell has at least one container-viewing window therein.

7. The improved syringe of claim 6 wherein said shell comprises an open mesh containing a plurality of said windows.

8. The improved syringe of claim 1 wherein at least one of said shell and said container contains means to facilitate intentional breakage of at least one of said needle and container to prevent its reuse.

9. The improved syringe of claim 8 wherein said shell and said container contain concentric alignable transverse grooves to facilitate said breakage.

10. The improved syringe of claim 7 wherein said container outer surface is transversely grooved in an area exposed when said shell is in said second position, thereby facilitating said breakage.

11. The improved syringe of claim 7 wherein said shell is sufficiently resilient and flexible to premit breaking of said needle by hand through said shell when said shell is in said second position.

12. The improved syringe of claim 1 wherein said needle is a nozzle intergral with the front end of said container.

13. The method of safely disposing of a syringe which has its ears in the pockets at the rear end of said container, as set forth in claim 1, including the steps of:
   (a) deforming the shell to form an oval shape to thereby cause said ears to come out of the pockets in the rear end of said container,
   (b) moving said shell so as to completely encase the needle while aligning said ears with the projections at the top end of said container,
   (c) removing pressure from the deformed shell to allow it to assume its undeformed state and thereby cause said ears to be received within the projections at the top end of said container,
   (d) transporting the encased needle to and depositing it in a trash receptacle.

14. The method of claim 13 wherein said container is broken before being deposited in said trash receptacle.

* * * * *